(12) United States Patent
Shimada et al.

(10) Patent No.: US 11,180,447 B2
(45) Date of Patent: Nov. 23, 2021

(54) METHOD FOR PRODUCING METHIONINE

(71) Applicant: SUMITOMO CHEMICAL COMPANY, LIMITED, Chuo-ku (JP)

(72) Inventors: Noriyuki Shimada, Niihama (JP); Takao Mizuno, Niihama (JP); Daisuke Yamashita, Niihama (JP)

(73) Assignee: SUMITOMO CHEMICAL COMPANY, LIMITED, Chuo-ku (JP)

( * ) Notice: Subject to any disclaimer, the term of this patent is extended or adjusted under 35 U.S.C. 154(b) by 0 days.

(21) Appl. No.: 16/771,892

(22) PCT Filed: Dec. 12, 2018

(86) PCT No.: PCT/JP2018/045602
§ 371 (c)(1),
(2) Date: Jun. 11, 2020

(87) PCT Pub. No.: WO2019/117180
PCT Pub. Date: Jun. 20, 2019

(65) Prior Publication Data
US 2021/0070704 A1    Mar. 11, 2021

(30) Foreign Application Priority Data
Dec. 13, 2017 (JP) .............................. JP2017-238230

(51) Int. Cl.
*C07C 319/20* (2006.01)
*C07C 319/28* (2006.01)
(Continued)

(52) U.S. Cl.
CPC ........ *C07C 319/20* (2013.01); *B01D 19/0005* (2013.01); *C07C 319/28* (2013.01); *C01C 1/12* (2013.01); *C07C 323/58* (2013.01)

(58) Field of Classification Search
None
See application file for complete search history.

(56) References Cited

U.S. PATENT DOCUMENTS 3,636,098 A * 1/1972 Shima et al. ........ C07D 233/76
562/559
4,319,044 A    3/1982 Matsumoto et al.
(Continued)

FOREIGN PATENT DOCUMENTS

CN    102311375 A    1/2012
CN    102659684 A    9/2012
(Continued)

OTHER PUBLICATIONS

International Search Report dated Mar. 19, 2019 in PCT/JP2018/045602, 2 pages.
(Continued)

*Primary Examiner* — Amy C Bonaparte
(74) *Attorney, Agent, or Firm* — Oblon, McClelland, Maier & Neustadt, L.L.P.

(57) ABSTRACT

An object of the present invention to provide a method for producing methionine with consideration given to the environment. The production method of the present invention comprises a removal step of blowing an inert gas into a liquid containing 5-(2-methylmercaptoethyl)hydantoin and thereby diffusing ammonia remaining in the liquid to obtain an emission gas containing the ammonia, and a recovery step of bringing the emission gas into contact with a washing liquid to recover ammonia contained in the emission gas.

4 Claims, 1 Drawing Sheet

(51) Int. Cl.
*C07C 323/58* (2006.01)
*B01D 19/00* (2006.01)
*C01C 1/12* (2006.01)

(56) References Cited

U.S. PATENT DOCUMENTS

| | | | |
|---|---|---|---|
| 2006/0016334 A1* | 1/2006 | Hasselbach | B01D 53/62 |
| | | | 95/235 |
| 2007/0246129 A1 | 10/2007 | Onishi et al. | |
| 2011/0319659 A1 | 12/2011 | Yoshikawa et al. | |
| 2014/0155652 A1 | 6/2014 | Yamashiro et al. | |
| 2015/0284323 A1 | 10/2015 | Chen et al. | |

FOREIGN PATENT DOCUMENTS

| | | |
|---|---|---|
| CN | 102796033 A | 11/2012 |
| CN | 103848765 A | 6/2014 |
| CN | 105671587 A | 6/2016 |
| CN | 106432018 A | 2/2017 |
| CN | 106565608 A | 4/2017 |
| EP | 2 759 537 A1 | 7/2014 |
| JP | 55-100358 A | 7/1980 |
| JP | 60-344 B2 | 1/1985 |
| JP | 2007-314507 A | 12/2007 |
| JP | 2012-12316 A | 1/2012 |
| JP | 2014-108956 A | 6/2014 |
| JP | 2015-526485 A | 9/2015 |

OTHER PUBLICATIONS

English translation of the International Preliminary Report on Patentability and Written Opinion of the International Searching Authority dated Jun. 16, 2020 in PCT/JP2018/045602, 6 pages.
Chinese Office Action dated Aug. 5, 2021 in corresponding Chinese application No. 201880080165.0 (with English Translation).

* cited by examiner

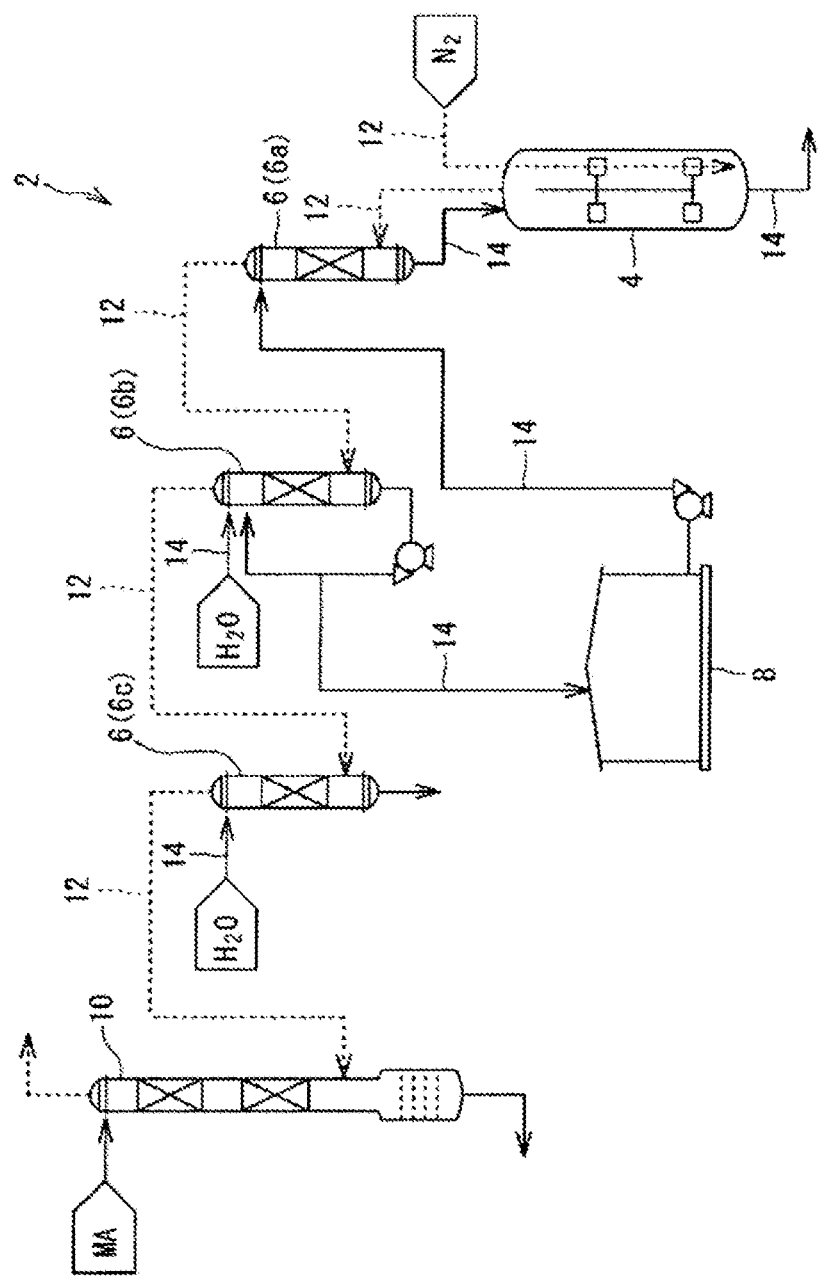

METHOD FOR PRODUCING METHIONINE

CROSS-REFERENCE TO RELATED APPLICATIONS

This Application is a national stage application of PCT/JP2018/045602 filed Dec. 12, 2018 which claims benefit of Japanese priority application 2017-238230, filed Dec. 13, 2017. The disclosure of both applications is incorporated herein by reference.

TECHNICAL FIELD

This patent application claims priority under the Paris Convention based on Japanese Patent Application No. 2017-238230 (filed on Dec. 13, 2017) incorporated herein by reference in its entirety.

The present invention relates to a method for producing methionine.

BACKGROUND ART

Methionine is obtained, for example by a hydrolysis reaction of 5-(2-methylmercaptoethyl)hydantoin as shown in the following reaction formula (1).

[Chem. 1]

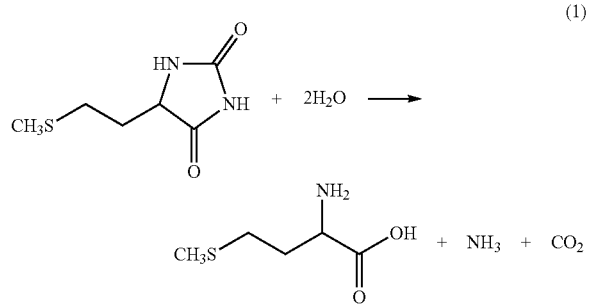

(1)

The 5-(2-methylmercaptoethyl)hydantoin described above is obtained, for example by a method of reacting 3-methylmercaptopropionaldehyde cyanohydrin with carbon dioxide and ammonia in water as shown by the following reaction formula (2). This 5-(2-methylmercaptoethyl)hydantoin can also be obtained by a method of reacting 3-methylmercaptopropionaldehyde with hydrocyanic acid, carbon dioxide, and ammonia.

[Chem. 2]

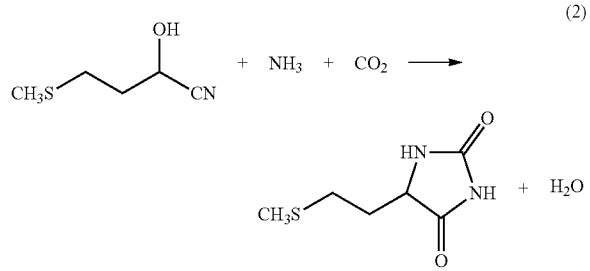

(2)

Methionine is a useful animal feed additive. From the viewpoint of quality improvement, production cost reduction, etc., various studies have been conducted on a method for producing methionine (e.g., Patent Document 1).

PRIOR ART DOCUMENT

Patent Document

Patent Document 1: Japanese Laid-Open Patent Publication No. 2014-108956

SUMMARY OF THE INVENTION

Problem to be Solved by the Invention

In a reaction for obtaining 5-(2-methylmercaptoethyl)hydantoin (hereinafter also referred to as a hydantoin reaction), an excess amount of ammonia is usually used. Therefore, unreacted ammonia remains in a liquid containing 5-(2-methylmercaptoethyl)hydantoin obtained by the hydantoin reaction. In production of methionine, the liquid containing 5-(2-methylmercaptoethyl)hydantoin is directly used in the hydrolysis reaction represented by the reaction formula (1). In Patent Document 1 described above, since the progress of the hydrolysis reaction is hindered if ammonia is contained in the liquid containing 5-(2-methylmercaptoethyl)hydantoin, the hydrolysis reaction is performed after ammonia is removed from this liquid.

In consideration of the impact on the environment, ammonia cannot directly be released into the atmosphere. In Patent Document 1 described above, how the removed ammonia was subsequently treated is not disclosed. In the production of methionine, consideration for the environment is strongly required so as not to discharge ammonia and damage the environment.

The present invention was conceived in view of the situations, and an object thereof is to provide a method for producing methionine with consideration given to the environment.

Means for Solving Problem

Focusing attention on the fact that ammonia is an essential component in the hydantoin reaction and intensively studying a technique that can ensure the consideration for the environment, the present inventors consequently have found a technique enabling reuse of ammonia remaining in a liquid containing 5-(2-methylmercaptoethyl)hydantoin obtained by reacting 3-methylmercaptopropionaldehyde and hydrocyanic acid, or a compound obtained by reacting 3-methylmercaptopropionaldehyde and hydrocyanic acid, with carbon dioxide and ammonia, thereby completing the present invention. Therefore, a method for producing methionine according to the present invention is a method for producing methionine comprising a hydantoin step of reacting 3-methylmercaptopropionaldehyde and hydrocyanic acid, or a compound obtained by reacting 3-methylmercaptopropionaldehyde and hydrocyanic acid, with carbon dioxide and ammonia to obtain a liquid containing 5-(2-methylmercaptoethyl)hydantoin, a hydrolysis step of hydrolyzing the 5-(2-methylmercaptoethyl)hydantoin, a crystallization step of introducing carbon dioxide into a liquid containing a methionine salt obtained at the hydrolysis step to precipitate methionine, and a separation step of separating a methionine slurry obtained at the crystallization step into solid and liquid, the method comprising:

a removal step of blowing an inert gas into the liquid containing the 5-(2-methylmercaptoethyl)hydantoin and thereby diffusing ammonia remaining in the liquid to obtain an emission gas containing the ammonia; and a recovery step of bringing the emission gas into contact with a washing liquid to recover ammonia contained in the emission gas, wherein the recovery step comprises at least one step selected from the group consisting of (1) a first step in which ammonium carbonate water is used as the washing liquid to dissolve ammonia contained in the emission gas into the ammonium carbonate water, and (2) a second step in which water is circulated and used as the washing liquid to dissolve ammonia contained in the emission gas into the water.

In this production method, in the first step or the second step, ammonia is recovered from the emission gas obtained in the removal step. The recovered ammonia can be reused, for example in the hydantoin step. In this production method, a gas discharged from a methionine production facility contains almost no ammonia. This production method enables the production of methionine with consideration given to the environment.

In this method for producing methionine, preferably, the recovery step comprises the first step and the second step.

In this production method, the first step and the second step are performed for the emission gas obtained in the removal step. In this production method, ammonia is sufficiently recovered from the emission gas. This production method enables the production of methionine with more consideration given to the environment.

In this method for producing methionine, more preferably, the second step is performed by using the emission gas that has been subjected to the first step.

According to this production method, since the second step is performed after the first step, ammonia can more efficiently be recovered from the emission gas obtained in the removal step. Moreover, water serving as the washing liquid is circulated for recovering ammonia in the second step, so that the amount of water used for recovering ammonia is effectively reduced. Furthermore, since the second step is performed for the emission gas from which ammonia has been recovered in the first step, a load required for the recovery of ammonia is reduced in the second step. In this production method, an ammonia recovery treatment can stably be performed. This production method enables the production of methionine with more consideration given to the environment.

In the method for producing methionine, further preferably, the recovery step comprises (3) a third step in which water is used as the washing liquid to dissolve ammonia contained in the emission gas into the water, and the third step is performed by using the emission gas that has been subjected to the second step.

In this production method, in the first step and the second step, most of the ammonia is recovered from the emission gas obtained in the removal step, so that ammonia is not contained in the emission gas subjected to the third step or, if ammonia is contained, the amount of ammonia contained in this emission gas is extremely small. In this production method, the impact of the gas discharged from the production facility on the environment is effectively suppressed.

In the method for producing methionine, preferably, the recovery step comprises at least the second step, and the circulation of water in the second step is continued until a concentration of ammonia dissolved in the water reaches 0.5 mass % or more.

According to this production method, the amount of water used for recovering ammonia can more effectively be reduced. This production method enables the production of methionine with sufficiently increased consideration given to the environment.

Effect of the Invention

As is clear from the above description, the production method of the present invention enables the production of methionine with consideration given to the environment.

BRIEF DESCRIPTION OF DRAWINGS

The drawing FIGURE is a schematic showing a portion of a facility used in a method for producing methionine according to an embodiment of the present invention.

MODE FOR CARRYING OUT THE INVENTION

The present invention will now be described in detail based on a preferred embodiment with appropriate reference to the drawing. In this description, conventionally known portions will not be described in detail except those necessary for describing the present invention.

[Method for Producing Methionine]

In the method for producing methionine according to an embodiment of the present invention, 3-methylmercaptopropionaldehyde (hereinafter also referred to as methionine aldehyde) is used as a starting material to obtain methionine. This production method comprises a hydantoin step, a hydrolysis step, a crystallization step, a separation step, a removal step, and a recovery step. Methionine aldehyde can be obtained, for example by reacting methyl mercaptan and acrolein.

[Hydantoin Step]

In the hydantoin step, methionine aldehyde and hydrocyanic acid, or a compound obtained, for example by reacting these components 3-methylmercaptopropionaldehyde cyanohydrin (hereinafter also referred to as methionine cyanohydrin), are reacted with carbon dioxide and ammonia in the presence of water to obtain a liquid containing 5-(2-methylmercaptoethyl)hydantoin (hereinafter also referred to as methionine hydantoin). Specifically, examples of the method for obtaining a liquid containing methionine hydantoin (hereinafter also referred to as a hydantoin liquid) include a method of reacting methionine aldehyde, hydrocyanic acid, carbon dioxide, and ammonia, and a method of reacting methionine cyanohydrin, carbon dioxide, and ammonia. In the present invention, carbon dioxide may be present in the form of carbonate ions and/or hydrogencarbonate ions. Ammonia may be present in the form of ammonium ions.

The reaction for obtaining methionine hydantoin from methionine cyanohydrin can be performed, for example by mixing methionine cyanohydrin with water in which carbon dioxide and ammonia are dissolved and heating the water. The reaction temperature is usually 50 to 90° C. The reaction time is usually 0.5 to 6 hours.

In the reaction for obtaining methionine hydantoin from methionine cyanohydrin, an amount of water used is usually 3 to 4 times by weight an amount of methionine cyanohydrin.

An amount of carbon dioxide used is usually 1 to 5 mols, preferably 1.5 to 3 mols, per mol of methionine cyanohydrin.

An amount of ammonia used is usually an excess amount of more than 2 mols, preferably 3 to 5 mols, per mol of methionine cyanohydrin.

When ammonium carbonate is used instead of carbon dioxide and ammonia, an amount of ammonium carbonate used is usually 0.7 to 3 times by weight, preferably 0.9 to 2 times by weight of an amount of methionine cyanohydrin.

A methionine hydantoin concentration of the hydantoin liquid is usually 1 to 50 mass %, preferably 10 to 20 mass %. In the present invention, the methionine hydantoin concentration can be measured by liquid chromatography.

In the hydantoin step, an excess amount of ammonia is usually used. Therefore, unreacted ammonia remains in the hydantoin liquid. This hydantoin liquid contains ammonia. An ammonia concentration of this hydantoin liquid is usually 2 to 7 mass %, preferably 3 to 6 mass %. The amount of ammonia contained in the hydantoin liquid is usually 1 to 4 mols, preferably 2 to 3 mols, per mol of methionine hydantoin. In the present invention, the ammonia concentration and the amount of ammonia are obtained by converting an amount of ammonium ions measured by ion chromatography into an amount of ammonia. Analysis conditions for measuring the amount of ammonium ions are as follows.

(Ion Chromatography Analysis Conditions)
Column: Dionex IonPac CS12A
Column size: 4 mm in inner diameter, 250 mm in length
Eluent: 20 mmol/L methanesulfonic acid The hydantoin liquid usually contains carbon dioxide in addition to ammonia. A carbon dioxide concentration of this hydantoin liquid is usually 2 to 7 mass %. The carbon dioxide concentration can be measured by gas chromatography.

The hydantoin liquid may contain methyl mercaptan in addition to methionine hydantoin, ammonia, and carbon dioxide. When the hydantoin liquid contains methyl mercaptan, a concentration of methyl mercaptan contained in the hydantoin liquid is usually 0.001 mass % to 1 mass %.

[Hydrolysis Step]

In the hydrolysis step, methionine hydantoin is hydrolyzed in the presence of an alkaline compound such as potassium hydroxide, sodium hydroxide, potassium carbonate, and potassium hydrogencarbonate. As a result, a liquid containing a methionine salt (hereinafter also referred to as a hydrolysis reaction liquid) is obtained. In the hydrolysis step, the pressure is usually set in a range of about 0.5 to 1.0 MPaG. The temperature is set in a range of 150 to 200° C.

[Crystallization Step]

In the crystallization step, carbon dioxide is introduced into the hydrolysis reaction liquid obtained in the hydrolysis step. As a result, methionine is precipitated, and a methionine slurry is obtained. In the crystallization step, the crystallization temperature is usually 0 to 50° C., preferably 10 to 30° C. The crystallization time is basically a time until carbon dioxide is saturated in the reaction liquid so that methionine is sufficiently precipitated and is usually 30 minutes to 24 hours.

[Separation Step]

In the separation step, the methionine slurry obtained in the crystallization step is subjected to solid-liquid separation into a methionine cake that is a solid component and a mother liquor that is a liquid component by a solid-liquid separator such as a centrifuge. In this production method, usually, the methionine cake obtained in this separation step is washed with washing water for purification, and the cake is then dried to obtain powder methionine as a product.

[Removal Step]

In this production method, the removal step is usually performed before the hydrolysis step. In this removal step, an inert gas is blown into the hydantoin liquid obtained in the hydantoin step. As described above, the hydantoin liquid contains ammonia. Therefore, by blowing the inert gas into the hydantoin liquid, i.e., by bubbling the hydantoin liquid with an inert gas, the ammonia remaining in the hydantoin liquid is diffused, and a gas containing the inert gas and ammonia (hereinafter also referred to as an emission gas) is discharged from the hydantoin liquid. As a result, ammonia is removed from the hydantoin liquid in this removal step. When the hydantoin liquid contains methyl mercaptan, the methyl mercaptan is also diffused by blowing the inert gas. Therefore, the emission gas discharged from the hydantoin liquid also contains methyl mercaptan.

Examples of the inert gas blown in this removal step comprise nitrogen gas, air, etc. An amount of the inert gas blown is usually 5 to 200 kg, preferably 10 to 100 kg, more preferably 20 to 60 kg per hour per 1000 kg of the hydantoin liquid.

In this removal step, from the viewpoint that the inert gas can be dispersed as fine bubbles in the hydantoin liquid, the blowing of the inert gas is preferably performed by using a sparger etc.

The temperature of the hydantoin liquid at the time of blowing of the inert gas is usually 30 to 70° C., preferably 40 to 60° C. The pH of this hydantoin liquid is usually 9 to 14. The time of blowing of the inert gas is usually 200 to 1200 minutes, preferably 400 to 800 minutes.

In the removal step, the emission gas containing ammonia is obtained by blowing the inert gas into the hydantoin liquid. In this production method, in the next recovery step, the emission gas obtained in the removal step is brought into contact with a washing liquid to recover ammonia contained in this emission gas.

[Recovery Step]

The drawing shows a portion of a facility 2 used in the method for producing methionine according to an embodiment of the present invention. A treatment of the emission gas containing ammonia obtained in the removal step is performed by using this facility 2.

The facility 2 comprises a reaction tank 4, three washing towers 6, a storage tank 8, and an absorption tower 10. In this production method, the hydantoin step is performed in the reaction tank 4. After the hydantoin step, the removal step is performed in the reaction tank 4.

In this facility 2, the three washing towers 6 are made up of a first washing tower 6a, a second washing tower 6b, and a third washing tower 6c. This facility 2 comprises the first washing tower 6a, the second washing tower 6b, and the third washing tower 6c as the washing towers 6.

In this facility 2, the reaction tank 4, the three washing towers 6, the storage tank 8, and the absorption tower 10 are respectively connected by gas pipes 12 through which gas flows and liquid pipes 14 through which liquid flows. This facility 2 is configured such that an emission gas discharged from the reaction tank 4 passes through the first washing tower 6a, the second washing tower 6b, and the third washing tower 6c in the order of the first washing tower 6a, the second washing tower 6b, and the third washing tower 6c. When the positions of the reaction tank 4, the three washing towers 6, and the absorption tower 10 are represented based on the flow of the emission gas, the first washing tower 6a is located downstream of the reaction tank 4. The second washing tower 6b is located downstream of the first washing tower 6a. The third washing tower 6c is located downstream of the second washing tower 6b. The absorption tower 10 is located downstream of the third washing tower 6c.

In this production method, as described above, in the removal step, a nitrogen gas is blown into the hydantoin liquid in the reaction tank 4 as the inert gas to remove methyl mercaptan and ammonia from the hydantoin liquid. The hydantoin liquid after removal of methyl mercaptan and ammonia is supplied to another reaction tank for performing the hydrolysis step. Subsequently, methionine cyanohydrin and ammonium carbonate water are supplied to the reaction vessel 4 for the next hydantoin reaction.

The recovery step of this production method comprises performing a step in which the ammonium carbonate water is used as a washing liquid in the first washing tower 6a to dissolve ammonia contained in the emission gas into the ammonium carbonate water (hereinafter also referred to as a first step).

[First Step]

In the first step, the emission gas is introduced into the first washing tower 6a from a lower portion of the first washing tower 6a. In this production method, the emission gas containing methyl mercaptan and ammonia discharged from the reaction tank 4 is introduced into the first washing tower 6a. This emission gas moves from the lower portion toward an upper portion in the first washing tower 6a and is discharged from the upper portion of the first washing tower 6a.

In this production method, the ammonium carbonate water used in the hydantoin reaction is prepared in the storage tank 8. In the first step, the ammonium carbonate water stored in the storage tank 8 is used as a washing liquid (hereinafter also referred to as a first washing liquid). This washing liquid is introduced into the first washing tower 6a from the upper portion of the first washing tower 6a. This washing liquid moves from the upper portion toward the lower portion in the first washing tower 6a and is discharged from the lower portion of the first washing tower 6a. In the first washing tower 6a, this washing liquid is allowed to pass through the first washing tower 6a without being circulated. In this production method, this washing liquid may be circulated and used in the first washing tower 6a so as to allow this washing liquid to repeatedly pass through the first washing tower 6a.

As described above, the washing liquid supplied to the first washing tower 6a, i.e., the first washing liquid, is the ammonium carbonate water. In other words, carbon dioxide and ammonia are dissolved in the first washing liquid.

In this production method, the carbon dioxide concentration of the first washing liquid is usually 5 mass % to 20 mass %. The ammonia concentration of the first washing liquid is 5 mass % to 20 mass %. The ammonia concentration is obtained by converting the amount of ammonium ions measured by ion chromatography described above into an amount of ammonia.

In this production method, the first washing liquid contains water. Examples of this water comprise pure water, ion-exchanged water, tap water, and industrial water.

In the first step, the emission gas and the washing liquid are introduced into the first washing tower 6a, and the emission gas is brought into contact with the washing liquid in the first washing tower 6a. As a result, the ammonia contained in the emission gas is dissolved into the washing liquid. Therefore, the ammonia concentration of the emission gas discharged from the first washing tower 6a is lower than the ammonia concentration of the emission gas introduced into the first washing tower 6a. The ammonia concentration of the washing liquid discharged from the first washing tower 6a is higher than the ammonia concentration of the washing liquid introduced into the first washing tower 6a. In the first step, the ammonia contained in the emission gas is recovered by the washing liquid in the first washing tower 6a.

As described above, the emission gas contains methyl mercaptan. However, since methyl mercaptan is not soluble in water, the washing liquid discharged from the first washing tower 6a does not contain methyl mercaptan.

In the first step, the temperature of the emission gas immediately before introduction into the first washing tower 6a is usually 70 to 80° C. The temperature of the emission gas immediately after discharge from the first washing tower 6a is usually 30 to 40° C. The temperature of the first washing liquid is usually 10 to 30° C. immediately before introduction into the first washing tower 6a. The flow rate of the first washing liquid introduced into the first washing tower 6a is usually set within a range of 1 to 10 times by weight the flow rate of the emission gas introduced into the first washing tower 6a.

The recovery step of this production method comprises performing a step in which water is circulated and used as a washing liquid in the second washing tower 6b to dissolve ammonia contained in the emission gas into the water (hereinafter also referred to as a second step).

[Second Step]

In the second step, the emission gas is introduced into the second washing tower 6b from a lower portion of the second washing tower 6b. In this production method, the emission gas discharged from the first washing tower 6a is introduced into the second washing tower 6b. This emission gas moves from the lower portion toward an upper portion in the second washing tower 6b and is discharged from the upper portion of the second washing tower 6b.

As described above, in the second step, water is used as a washing liquid (hereinafter also referred to as a second washing liquid). This washing liquid is introduced into the second washing tower 6b from the upper portion of the second washing tower 6b. The washing liquid moves from the upper portion toward the lower portion in the second washing tower 6b and is discharged from the lower portion of the second washing tower 6b.

In this production method, the water serving as the second washing liquid introduced into the second washing tower 6b is not particularly limited. Examples of this water comprise pure water, ion-exchanged water, tap water, and industrial water.

In this production method, also in the second step, the washing liquid and the emission gas are introduced so that the washing liquid and the emission gas are brought into contact with each other. As a result, the ammonia contained in the emission gas is dissolved into the washing liquid. Therefore, the ammonia concentration of the emission gas discharged from the second washing tower 6b is lower than the ammonia concentration of the emission gas introduced into the second washing tower 6b. The ammonia concentration of the washing liquid discharged from the second washing tower 6b is higher than the ammonia concentration of the washing liquid introduced into the second washing tower 6b. Thus, also in the second step, the ammonia contained in the emission gas is recovered into the washing liquid.

In this production method, the washing liquid is circulated and used in the second washing tower 6b. As a result, the washing liquid is allowed to repeatedly pass through the second washing tower 6b. When the ammonia concentration of the washing liquid reaches a predetermined concentration or more, this washing liquid is supplied to the storage tank 8, and water is freshly introduced as the washing liquid into the second washing tower 6b. Since the washing liquid is circulated and used in the second washing tower 6b in this way, the amount of the washing liquid used can be reduced.

In this production method, the emission gas subjected to an ammonia recovery treatment in the first washing tower 6a is introduced into the second washing tower 6b. In this production method, a load required for the recovery of ammonia in the second washing tower 6b is reduced. In the second washing tower 6b, the ammonia recovery treatment can stably be performed.

In this production method, the temperature of the emission gas immediately before introduction into the second washing tower 6b is usually 30 to 40° C. The temperature of the emission gas immediately after discharge from the second washing tower 6b is usually 20 to 35° C. The temperature of the second washing liquid is usually 10 to 30° C. immediately before introduction into the second washing tower 6b. The flow rate of the second washing liquid introduced into the second washing tower 6b is usually set within a range of 1 to 10 times by weight the flow rate of the emission gas introduced into the second washing tower 6b.

The recovery step of this production method comprises performing a step in which water is used as a washing liquid in the third washing tower 6c to dissolve ammonia contained in the emission gas into the water (hereinafter also referred to as a third step).

[Third Step]

In the third step, the emission gas is introduced into the third washing tower 6c from a lower portion of the third washing tower 6c. In this production method, the emission gas discharged from the second washing tower 6b is introduced into the third washing tower 6c. This emission gas moves from the lower portion toward an upper portion in the third washing tower 6c and is discharged from the upper portion of the third washing tower 6c.

As described above, in this third step, water is used as a washing liquid (hereinafter also referred to as a third washing liquid). This washing liquid is introduced into the third washing tower 6c from the upper portion of the third washing tower 6c. This washing liquid moves from the upper portion to the lower portion in the third washing tower 6c and is discharged from the lower portion of the third washing tower 6c.

In this production method, the water serving as the third washing liquid introduced into the third washing tower 6c is not particularly limited. Examples of this water comprise pure water, ion-exchanged water, tap water, and industrial water.

In this production method, also in the third step, the washing liquid and the emission gas are introduced so that the washing liquid and the emission gas are brought into contact with each other. As a result, the ammonia contained in the emission gas is dissolved into the washing liquid. Therefore, the ammonia concentration of the emission gas discharged from the third washing tower 6c is lower than the ammonia concentration of the emission gas introduced into the third washing tower 6c. The ammonia concentration of the washing liquid discharged from the third washing tower 6c is higher than the ammonia concentration of the washing liquid introduced into the third washing tower 6c. Thus, also in the third step, the ammonia contained in the emission gas is recovered into the washing liquid.

In this production method, the temperature of the emission gas immediately before introduction into the third washing tower 6c is usually 20 to 35° C. The temperature of the emission gas immediately after discharge from the third washing tower 6c is usually 15 to 30° C. The temperature of the third washing liquid is usually 10 to 30° C. immediately before introduction into the third washing tower 6c. The flow rate of the third washing liquid introduced into the third washing tower 6c is usually set within a range of 1 to 10 times by weight the flow rate of the emission gas introduced into the third washing tower 6c.

In this production method, the emission gas discharged from the third washing tower 6c is introduced into the absorption tower 10 from a lower portion of the absorption tower 10. The emission gas moves from the lower portion toward an upper portion in the absorption tower 10 and is discharged from the upper portion of the absorption tower 10.

As described above, the emission gas contains methyl mercaptan. Therefore, in this production method, methionine aldehyde is introduced into the absorption tower 10 from the upper portion of the absorption tower 10 so as to recover the methyl mercaptan. This methionine aldehyde moves from the upper portion toward the lower portion in the absorption tower 10 and is discharged from the lower portion of the absorption tower 10 together with methyl mercaptan. As a result, methyl mercaptan is recovered from the emission gas. The recovered methyl mercaptan is reused as a raw material in the production of methionine. In in the drawing "MA" means methionine aldehyde.

In this production method, the washing liquid containing ammonia recovered from the emission gas in the first washing tower 6a is supplied to the reaction tank 4. In this production method, the ammonia recovered from the emission gas in the first step is used in the hydantoin step.

In this production method, the washing liquid containing ammonia recovered from the emission gas in the second washing tower 6b is used in the storage tank 8 for preparing the ammonium carbonate water. As described above, in this production method, the ammonium carbonate water stored in the storage tank 8 is supplied to the first washing tower 6a as the washing liquid. The washing liquid discharged from the first washing tower 6a is supplied to the reaction tank 4. Therefore, in this production method, not only the ammonia recovered from the emission gas in the first washing tower 6a but also the ammonia recovered from the emission gas in the second washing tower 6b is supplied to the reaction tank 4. In this production method, the ammonia recovered from the emission gas in the first step and the second step is used in the hydantoin step.

In this production method, the ammonium carbonate water stored in the storage tank 8 may directly be supplied to the reaction tank 4. In this case, the ammonia recovered in the second step is supplied to the reaction tank 4 without going through the first washing tower 6a.

In this production method, for example, the ammonia recovered in the third step by supplying the washing liquid discharged from the third washing tower 6c to the reaction tank 4 can also be used in the hydantoin step performed in the reaction tank 4. On the other hand, the washing liquid discharged from the third washing tower 6c has a low ammonia concentration and therefore can be made harmless by a biological treatment. Thus, the washing liquid discharged from the third washing tower 6c can be biologically-treated and drained.

In this production method, the washing tower 6 disposed in the facility 2 may be made up of only the first washing tower 6a. In this case, the emission gas discharged from the first washing tower 6a is introduced into the absorption tower 10. The washing liquid discharged from the first washing tower 6a is supplied to the reaction tank 4.

In this production method, the washing tower 6 may be made up of only the second washing tower 6b. In this case, the emission gas discharged from the reaction tank 4 is introduced into the second washing tower 6b. The emission gas discharged from the second washing tower 6b is introduced into the absorption tower 10. Additionally, the washing liquid after recovering ammonia from the emission gas in the second washing tower 6b is used for preparing the ammonium carbonate water in the storage tank 8, and this ammonium carbonate water is supplied to the reaction tank 4.

In this production method, in the first step or the second step, ammonia is recovered from the emission gas obtained in the removal step. As described above, the recovered ammonia can be reused, for example in the hydantoin step. In this production method, the gas discharged from the methionine production facility contains almost no ammonia. This production method enables the production of methionine with consideration given to the environment.

In this method for producing methionine, the recovery step preferably comprises the first step and the second step. With this configuration, the first step and the second step are performed for the emission gas obtained in the removal step. In this production method, ammonia is sufficiently recovered from the emission gas. This production method enables the production of methionine with more consideration given to the environment.

In this method for producing methionine, more preferably, the second step is performed for the emission gas after being subjected to the first step. With this configuration, since the second step is performed after the first step, ammonia can more efficiently be recovered from the emission gas obtained in the removal step in this production method. Moreover, water serving as the washing liquid is circulated for recovering ammonia in the second step, so that the amount of water used for recovering ammonia is effectively reduced. Furthermore, since the second step is performed for the emission gas from which ammonia has been recovered in the first step, the load required for the recovery of ammonia is reduced in the second step. In this production method, the ammonia recovery treatment can stably be performed. This production method enables the production of methionine with more consideration given to the environment.

In this method for producing methionine, more preferably, the recovery step comprises the third step, and the third step is performed for the emission gas after being subjected to the second step. In the first step and the second step, most of the ammonia is recovered from the emission gas obtained in the removal step, so that ammonia is not contained in the emission gas subjected to the third step or, if ammonia is contained, the amount of ammonia contained in this emission gas is extremely small. In this production method, since ammonia is also recovered from the emission gas in the third step, the impact of the gas discharged from the production facility on the environment is sufficiently suppressed.

In this method for producing methionine, the recovery step suitably comprises at least the second step, and the circulation of water in the second step is preferably continued until the concentration of ammonia dissolved in this water reaches 0.5 mass % or more. With such a configuration, the amount of water used for recovering ammonia can more effectively be reduced. This production method enables the production of methionine with sufficiently increased consideration given to the environment. From this viewpoint, the circulation of water in the second step is preferably continued until the concentration of ammonia dissolved in this water reaches 1 mass % or more. The concentration of ammonia dissolved in this water is preferably 10 mass % or less.

As is clear from the above description, the production method of the present invention enables the production of methionine with consideration given to the environment.

EXAMPLES

The present invention will hereinafter be described in more detail with examples etc.; however, the present invention is not limited only to these examples.

Example 1

[Production of Methionine]

Methionine aldehyde and hydrocyanic acid were reacted at normal temperature under ordinary pressure to synthesize methionine cyanohydrin. Ammonium carbonate was reacted with this methionine cyanohydrin in water at 75° C. for 2.5 hours to obtain a liquid containing 15 mass % methionine hydantoin and 3.6 mass % ammonia, i.e., a hydantoin liquid.

A nitrogen gas was blown into the hydantoin liquid as an inert gas. A liquid (potassium concentration: about 7.5 mass %) obtained by mixing a basic potassium compound containing potassium carbonate, potassium hydrogencarbonate, and potassium hydroxide with the hydantoin liquid after the blowing of the nitrogen gas was continuously supplied from an upper portion of an autoclave (supply rate: 700 g/hour), and a hydrolysis reaction was performed while maintaining the pressure at 1.0 MPaG and the temperature at 180° C. to obtain a liquid containing a methionine salt (hereinafter referred to as a hydrolysis reaction liquid).

Into the hydrolysis reaction liquid, carbon dioxide was introduced at 0.35 MPaG and 20° C. As a result, methionine was precipitated, and a methionine slurry was obtained.

The methionine slurry was subjected to solid-liquid separation using a centrifugal filter (KOKUSAN Co. Ltd., H-112). Specifically, the methionine slurry was poured at 600 g/min into the centrifugal filter rotated at 1700 rpm so that crude methionine stuck to a filter cloth. Subsequently, the number of revolutions was set to 3800 rpm to shake off water for 2 minutes. As a result, the methionine slurry was separated into solid and liquid to obtain a methionine cake and a mother liquor. The pure methionine content in the methionine cake measured was 49.0 g (converted from HPLC measurement).

The methionine cake was washed by spraying a washing liquid for purification and then dried under a slightly reduced pressure at a temperature of 85 to 105° C. to obtain powder methionine as a product (purity=99.6%, yield=97%). The mother liquor was introduced into a concentrator and heated at 115° C. and then 140° C. under an increased pressure of 0.2 MPaG for concentration. Although not described in detail, the concentrated liquid obtained by this concentration was also subjected to crystallization and solid-liquid separation to recover methionine contained in the concentrated liquid.

In the facility having the configuration shown in the drawing, an emission gas containing ammonia obtained by blowing the nitrogen gas into the hydantoin liquid in the reaction tank was introduced into the first washing tower, the second washing tower, and the third washing tower in this order to recover the ammonia contained in this emission gas. Ammonium carbonate water was used as the first washing liquid. Water was used as the second washing liquid and the third washing liquid. Water was circulated and used as the second washing liquid. In this example, the ammonia recovered in the first washing tower and the second washing tower was supplied to the reaction tank. In this example, the amount of nitrogen gas blown was set to 4.4 kg per hour per 1000 kg of the hydantoin liquid. The flow rate of the first washing liquid introduced into the first washing tower was set to 5.0 times by weight the flow rate of the emission gas introduced into the first washing tower. The flow rate of the second washing liquid introduced into the second washing tower was set to 5.7 times by weight the flow rate of the emission gas introduced into the second washing tower. The flow rate of the third washing liquid introduced into the third washing tower was set to 4.0 times by weight the flow rate of the emission gas introduced into the third washing tower.

[Ammonia Recovery Rate]

An amount of ammonia contained in the emission gas introduced into each of the washing towers and an amount of ammonia recovered in each of the washing towers were measured. An ammonia recovery rate (%) in each of the washing towers was obtained based on the following equation:

(ammonia recovery rate)=(amount of ammonia recovered in a washing tower)/(amount of ammonia introduced into the washing tower)×100.

As a result, the ammonia recovery rate of the first washing tower was 98.3%, the ammonia recovery rate of the second washing tower was 98.1%, and the ammonia recovery rate of the third washing tower was 98.0%. The sum of the amounts of ammonia recovered in the first washing tower and the second washing tower results in the recovery rate of 99.96%. This evaluation result reveals that, in the present invention, almost all the ammonia contained in the emission gas obtained by blowing the inert gas into the hydantoin liquid obtained by the hydantoin reaction is recovered, and that the recovered ammonia is reused for the production of methionine, i.e., that the production method of the present invention enables the production of methionine with consideration given to the environment.

INDUSTRIAL APPLICABILITY

The method for producing methionine described above can provide a technique for producing methionine with consideration given to the environment.

EXPLANATIONS OF LETTERS OR NUMERALS 2 facility
4 reaction tank
6 washing tower
6a first washing tower
6b second washing tower
6c third washing tower
8 storage tank
10 absorption tower
12 gas pipe
14 liquid pipe

The invention claimed is:

1. A method for producing methionine, comprising:
reacting 3-methylmercaptopropionaldehyde and hydrocyanic acid, or a compound obtained by reacting 3-methylmercaptopropionaldehyde and hydrocyanic acid, with carbon dioxide and ammonia to obtain a liquid containing 5-(2-methylmercaptoethyl)hydantoin;
introducing an inert gas into the liquid containing the 5-(2-methylmercaptoethyl)hydantoin and thereby diffusing ammonia remaining in the liquid to obtain an emission gas containing the ammonia;
hydrolyzing the 5-(2-methylmercaptoethyl)hydantoin to obtain a hydrolysis reaction liquid;
introducing carbon dioxide into the hydrolysis reaction liquid to precipitate methionine;
separating a methionine precipitate from the liquid containing the methionine into a methionine containing solid and a liquid;
and
recovering ammonia contained in the emission gas, the recovering comprising contacting the emission gas with a washing liquid,
wherein
the recovering comprises a first recovery treatment and a second recovery treatment,
the first recovery treatment applies ammonium carbonate water as the washing liquid to dissolve ammonia contained in the emission gas into the ammonium carbonate water, and
the second recovery treatment circulates and applies water as the washing liquid to dissolve ammonia contained in the emission gas into the water.

2. The method according to claim 1, wherein the second recovery treatment is performed on the emission gas that has been subjected to the first recovery treatment.

3. The method according to claim 2, wherein
the recovering comprises
a third recovery treatment which applies water as the washing liquid to dissolve ammonia contained in the emission gas into the water, and
the third recovery treatment is performed on the emission gas after being subjected to the second recovery treatment.

4. The method according to claim 1, wherein
the water is circulated in the second recovery treatment until a concentration of ammonia dissolved in the water reaches 0.5 mass % or more.

* * * * *